United States Patent
Sharma

(10) Patent No.: US 7,906,675 B2
(45) Date of Patent: Mar. 15, 2011

(54) COMPOUNDS FOR THE TREATMENT OF METABOLIC DISORDERS

(75) Inventor: Shalini Sharma, Gaithersburg, MD (US)

(73) Assignee: Wellstat Therapeutics Corporation, Gaithersburg, MD (US)

( * ) Notice: Subject to any disclaimer, the term of this patent is extended or adjusted under 35 U.S.C. 154(b) by 804 days.

(21) Appl. No.: 10/566,302

(22) PCT Filed: Aug. 16, 2004

(86) PCT No.: PCT/US2004/026561
§ 371 (c)(1),
(2), (4) Date: Mar. 1, 2007

(87) PCT Pub. No.: WO2005/018628
PCT Pub. Date: Mar. 3, 2005

(65) Prior Publication Data
US 2007/0282003 A1    Dec. 6, 2007

Related U.S. Application Data

(60) Provisional application No. 60/496,533, filed on Aug. 20, 2003.

(51) Int. Cl.
C07C 69/76     (2006.01)
C07C 119/00    (2006.01)
C07D 211/70    (2006.01)

(52) U.S. Cl. ............... 560/8; 560/19; 560/39; 560/75; 546/1; 546/339

(58) Field of Classification Search ............... 560/8, 19, 560/39, 75; 541/1, 329
See application file for complete search history.

(56) References Cited

U.S. PATENT DOCUMENTS

| | | |
|---|---|---|
| 6,858,602 B2 | 2/2005 | Sharma et al. |
| 6,916,848 B2 | 7/2005 | Sharma |
| 6,924,314 B2 | 8/2005 | Sharma et al. |
| 6,946,491 B2 | 9/2005 | Sharma et al. |
| 7,012,071 B2 | 3/2006 | Sharma et al. |
| 7,041,659 B2 | 5/2006 | Sharma |
| 7,045,541 B2 | 5/2006 | Sharma |
| 7,101,910 B2 | 9/2006 | Sharma |
| 2005/0090555 A1 | 4/2005 | Sharma et al. |
| 2005/0256333 A1 | 11/2005 | Sharma et al. |
| 2006/0014784 A1 | 1/2006 | Hodge et al. |
| 2006/0035970 A1 | 2/2006 | Hodge et al. |
| 2006/0247309 A1 | 11/2006 | Hodge et al. |
| 2007/0105955 A1 | 5/2007 | Hodge et al. |
| 2007/0105958 A1 | 5/2007 | Sharma et al. |
| 2007/0173544 A1 | 7/2007 | Hodge et al. |

FOREIGN PATENT DOCUMENTS

| | | |
|---|---|---|
| FR | 5.035 M | 5/1967 |
| WO | WO02/100341 | 12/2002 |

OTHER PUBLICATIONS

Pending (as of Aug. 20, 2007) claims from U.S. Appl. No. 11/841,508.
Pending (as of Jul. 2, 2007) claims from U.S. Appl. No. 11/772,501.
Pending (as of Jul. 2, 2007) claims from U.S. Appl. No. 11/772,504.
Pending (as of Jul. 2, 2007) claims from U.S. Appl. No. 11/772,511.
Pending (as of Jul. 2, 2007) claims from U.S. Appl. No. 11/772,515.
Pending (as of Jul. 2, 2007) claims from U.S. Appl. No. 11/772,520.
Pending (as of Jul. 2, 2007) claims from U.S. Appl. No. 11/772,556.
Pending (as of Jul. 2, 2007) claims from U.S. Appl. No. 11/772,560.
Pending (as of Aug. 24, 2007) claims from U.S. Appl. No. 11/844,431.
Pending (as of Aug. 24, 2007) claims from U.S. Appl. No. 11/844,432.
Pending (as of Aug. 20, 2007) claims from U.S. Appl. No. 11/841,489.
Pending (as of Sep. 19, 2007) claims from U.S. Appl. No. 11/909,120.
Younis, et al., "The prevention of type 2 diabetes mellitus: recent advances", QJ Med., vol. 97, pp. 451-455, 2004.
Goff, et al., "Prevention of Cardiovascular Disease in Persons with type 2 diabetes Mellitus: Current Knowledge and Rational for the Action to Control Cardiovascular Risk in Diabetes (ACCORD) Trial", AM J Cardiol., 99(12A): S4-S20, 2007. (Abstract).
Knowler, et al., "Perspectives in Diabetes: Preventing Non-Insulin-Dependent Diabetes", Diabetes, vol. 44, pp. 483-488, 1995.
Shinkai, et al., "Bis(2-(Acylamino)phenyl) Disulfides, 2-(Acylamino)benzenethiols, and S-(2-(Acylamino)phenyl) Alkanethioates as Novel Inhibitors of Cholesteryl Ester Transfer Protein", J. Med. Chem., (2000), vol. 43, pp. 3566-3572. Bebernitz, et al., "Reduction in Glucose Levels in STZ Diabetic Rats by 4-(2,2-Dimethyl-1-oxopropyl)benzoic Acid: A Prodrug Approach for Targeting the Liver", J. Med. Chem., (2001), vol. 44, pp. 512-523.
Beilstein Registry No. 2676894; referencing Overberger, et al., Journal of Organic Chemistry, 27: 3539-3545, 1962. (XP002518195).
Beilstein Registry No. 2675571; referencing Overberger, et al., Journal of Organic Chemistry; 27: 3539-3545, 1962. (XP0025181896).

*Primary Examiner* — Janet L. Andres
(74) *Attorney, Agent, or Firm* — Lewis J. Kreisler

(57) ABSTRACT

A biologically active agent, wherein the agent is a compound of the formula:

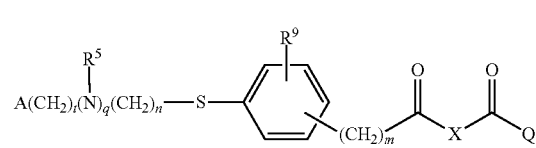

Wherein A, $R^5$, $R^9$, X, Q and n, m, q are defined herein below.

3 Claims, No Drawings

COMPOUNDS FOR THE TREATMENT OF METABOLIC DISORDERS

REFERENCE TO PRIOR APPLICATIONS

This is the national phase under 35 U.S.C. §371 of International Application No. PCT/US2004/026561, having an international filing date of Aug. 16, 2004. This application claims priority of U.S. Provisional Application No. 60/496,533, filed Aug. 20, 2003, the contents of which are hereby incorporated by reference.

BACKGROUND OF THE INVENTION

Diabetes mellitus is a major cause of morbidity and mortality. Chronically elevated blood glucose leads to debilitating complications: nephropathy, often necessitating dialysis or renal transplant; peripheral neuropathy; retinopathy leading to blindness; ulceration of the legs and feet, leading to amputation; fatty liver disease, sometimes progressing to cirrhosis; and vulnerability to coronary artery disease and myocardial infarction.

There are two primary types of diabetes. Type I, or insulin-dependent diabetes mellitus (IDDM) is due to autoimmune destruction of insulin-producing beta cells in the pancreatic islets. The onset of this disease is usually in childhood or adolescence. Treatment consists primarily of multiple daily injections of insulin, combined with frequent testing of blood glucose levels to guide adjustment of insulin doses, because excess insulin can cause hypoglycemia and consequent impairment of brain and other functions.

Type II, or noninsulin-dependent diabetes mellitus (NIDDM) typically develops in adulthood. NIDDM is associated with resistance of glucose-utilizing tissues like adipose tissue, muscle, and liver, to the actions of insulin. Initially, the pancreatic islet beta cells compensate by secreting excess insulin. Eventual islet failure results in decompensation and chronic hyperglycemia. Conversely, moderate islet insufficiency can precede or coincide with peripheral insulin resistance. There are several classes of drugs that are useful for treatment of NIDDM: 1) insulin releasers, which directly stimulate insulin release, carrying the risk of hypoglycemia; 2) prandial insulin releasers, which potentiate glucose-induced insulin secretion, and must be taken before each meal; 3) biguanides, including metformin, which attenuate hepatic gluconeogenesis (which is paradoxically elevated in diabetes); 4) insulin sensitizers, for example the thiazolidinedione derivatives rosiglitazone and pioglitazone, which improve peripheral responsiveness to insulin, but which have side effects like weight gain, edema, and occasional liver toxicity; 5) insulin injections, which are often necessary in the later stages of NIDDM when the islets have failed under chronic hyperstimulation.

Insulin resistance can also occur without marked hyperglycemia, and is generally associated with atherosclerosis, obesity, hyperlipidemia, and essential hypertension. This cluster of abnormalities constitutes the "metabolic syndrome" or "insulin resistance syndrome". Insulin resistance is also associated with fatty liver, which can progress to chronic inflammation (NASH; "nonalcoholic steatohepatitis"), fibrosis, and cirrhosis. Cumulatively, insulin resistance syndromes, including but not limited to diabetes, underlie many of the major causes of morbidity and death of people over age 40.

Despite the existence of such drugs, diabetes remains a major and growing public health problem. Late stage complications of diabetes consume a large proportion of national health care resources. There is a need for new orally active therapeutic agents which effectively address the primary defects of insulin resistance and islet failure with fewer or milder side effects than existing drugs.

Currently there are no safe and effective treatments for fatty liver disease. Therefore such a treatment would be of value in treating this condition.

WO 02/100341 (Wellstat Therapeutics Corp.) discloses certain compounds having oxygen in place of sulfur, for example 4-(3-(2,6-Dimethylbenzyloxy)phenyl)-4-oxobutyric acid.

SUMMARY OF THE INVENTION

This invention provides a biologically active agent as described below. This invention provides the use of the biologically active agent described below in the manufacture of a medicament for the treatment of insulin resistance syndrome, diabetes, cachexia, hyperlipidemia, fatty liver disease, obesity, atherosclerosis or arteriosclerosis. This invention provides methods of treating a mammalian subject with insulin resistance syndrome, diabetes, cachexia, hyperlipidemia, fatty liver disease, obesity, atherosclerosis or arteriosclerosis comprising administering to the subject an effective amount of the biologically active agent described below. This invention provides a pharmaceutical composition comprising the biologically active agent described below and a pharmaceutically acceptable carrier.

The biologically active agent in accordance with this invention is a compound of Formula I:

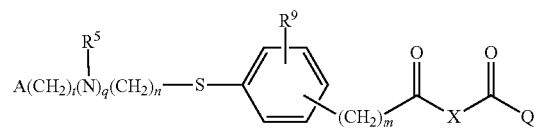

wherein n is 1 or 2; m is 0 or 1; q is 0 or 1; t is 0 or 1; $R^5$ is alkyl having from 1 to 3 carbon atoms; $R^9$ is hydrogen, halo, alkyl having from 1 to 3 carbon atoms, or alkoxy having from 1 to 3 carbon atoms;

A is phenyl, unsubstituted or substituted by 1 or 2 groups selected from: halo, alkyl having 1 or 2 carbon atoms, perfluoromethyl, alkoxy having 1 or 2 carbon atoms, and perfluoromethoxy; or cycloalkyl having from 3 to 6 ring carbon atoms wherein the cycloalkyl is unsubstituted or one or two ring carbons are independently mono-substituted by methyl or ethyl; or a 5 or 6 membered heteroaromatic ring having 1 or 2 ring heteroatoms selected from N, S and O and the heteroaromatic ring is covalently bound to the remainder of the compound of formula I by a ring carbon; and X is —CH$_2$—, Q is —OR$^1$ and R$^1$ is methyl or ethyl; or X is —CH$_2$CR$^{12}$R$^{13}$— or —CH$_2$CH(NHAc)— wherein each of R$^{12}$ and R$^{13}$ is independently hydrogen or methyl, Q is OR$^1$ and R$^1$ is hydrogen or alkyl having from 1 to 7 carbon atoms; or X is —CH$_2$CH$_2$— and Q is NR$^{10}$R$^{11}$ wherein one of R$^{10}$ and R$^{11}$ is hydrogen, alkyl having from 1 to 3 carbon atoms or hydroxy, and the other is hydrogen;

or when R$^1$ is hydrogen, a pharmaceutically acceptable salt of the compound.

The biologically active agents described above have activity in the biological activity assay described below, which is an established animal model of human diabetes and insulin resistance syndrome. Therefore such agents would be useful in the treatment of diabetes and insulin resistance syndrome. The exemplified compound demonstrated activity in such assay.

DETAILED DESCRIPTION OF THE INVENTION

Definitions

As used herein the term "alkyl" means a linear or branched-chain alkyl group. An alkyl group identified as having a certain number of carbon atoms means any alkyl group having the specified number of carbons. For example, an alkyl having three carbon atoms can be propyl or isopropyl; and alkyl having four carbon atoms can be n-butyl, 1-methylpropyl, 2-methylpropyl or t-butyl.

As used herein the term "halo" refers to one or more of fluoro, chloro, bromo, and iodo.

As used herein the term "perfluoro" as in perfluoromethyl or perfluoromethoxy, means that the group in question has fluorine atoms in place of all of the hydrogen atoms.

As used herein "Ac" refers to the group $CH_3C(O)$—.

Certain chemical compounds are referred to herein by their chemical name or by the two-letter code shown below. Compound CS is included within the scope of Formula I shown above.

CS 4-(4-[(2,6-Dimethylbenzyl)-thio]-phenyl)-4-oxobutyric acid

As used herein the transitional term "comprising" is open-ended. A claim utilizing this term can contain elements in addition to those recited in such claim.

Compounds of the Invention

In an embodiment of the agent, use, method or pharmaceutical composition described above, n is 1; q is 0; t is 0; $R^9$ is hydrogen; and A is phenyl, unsubstituted or substituted by 1 or 2 groups selected from: halo, alkyl having 1 or 2 carbon atoms, perfluoromethyl, alkoxy having 1 or 2 carbon atoms, and perfluoromethoxy. In a more specific embodiment, A is 2,6-dimethylphenyl. Examples of such compounds include Compound CS.

In a preferred embodiment of the biologically active agent of this invention, the agent is in substantially (at least 98%) pure form.

Reaction Schemes

The compound of formula I where X is —$CH_2CR^{12}R^{13}$—, q is 0, m is 0 or 1, t is 0 or 1, and n is 1 or 2, $R^9$ is hydrogen, halo, alkoxy having 1 to 3 carbon atoms or alkyl having 1 to 3 carbon atoms, Q is $OR^1$ where $R^1$ is hydrogen or alkyl having from 1 to 7 carbon atoms, i.e. compounds of formula:

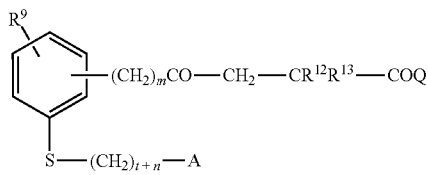

wherein A is described as above, $R^{12}$ and $R^{13}$ is independently hydrogen or methyl, can be prepared via Reaction Scheme 1.

In Reaction Scheme 1, A, t, n, $R^{12}$, $R^{13}$ and $R^9$ are as above. $R^6$ is an alkyl group containing from 1 to 7 carbon atoms, and Y is a halo group.

The compound of formula IV can be prepared by alkylating the compound of formula II with a compound of formula III via reaction of step (a) by using suitable base such as potassium carbonate, sodium hydride, triethylamine, pyridine and the like. Generally, the reaction is carried out in an inert solvent such as tetrahydrofuran, dichloromethane, N,N-dimethylformamide and the like. Any conditions conventional for the preparation of thioethers can be utilized to carry out the reaction of step (a).

The compound of formula IV is converted to the compound of formula VI via reaction of step (b) by alkylating the compound of formula IV with the compound of formula V. This reaction is carried out utilizing a conventional base that converts acetophenone to 3-keto ester (i.e. gamma-keto ester). In carrying out this reaction it is generally preferred to utilize alkali metal salts of hexamethyldisilazane such as lithium bis(trimethylsilyl)amide.

Generally, the reaction is carried out in an inert solvent such as tetrahydrofuran: 1,3-dimethyl-3,4,5,6-tetrahydro-2 (1H)-pyrimidinone (5:1). Generally, the reaction is carried out at temperatures of from –65° C. to 25° C. The product can be isolated and purified by techniques such as extraction, evaporation, chromatography, and recrystallization.

The compound of formula VI is the compound of formula I where $R^1$ is an alkyl group containing from 1 to 7 carbon atoms. The compound of formula VI can be converted to the free acid i.e. the compound of formula I where $R^1$ is H by ester hydrolysis. Any conventional method of ester hydrolysis will produce the compound of formula I where $R^1$ is H.

Scheme 1

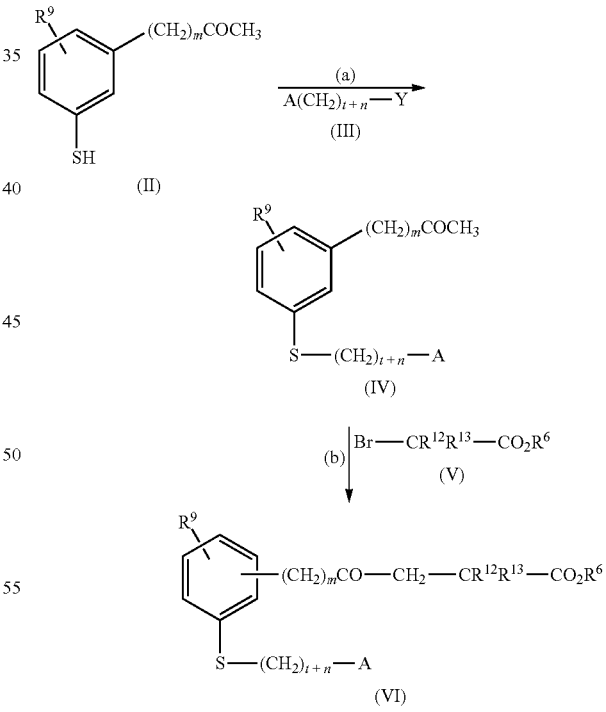

The compound of formula I where X is —$CH_2CR^{12}R^{13}$—, q is 1, m is 0 or 1, t is 0 or 1, n is 1 or 2, $R^9$ is hydrogen, halo, alkoxy having 1 to 3 carbon atoms or alkyl having 1 to 3 carbon atoms, Q is $OR^1$ where $R^1$ is hydrogen or alkyl having from 1 to 7 carbon atoms and $R^5$ is an alkyl group having 1 to 3 carbon atoms, i.e. compounds of formula:

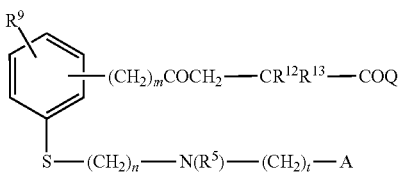

wherein A is described as above, $R^{12}$ and $R^{13}$ is independently hydrogen or methyl, can be prepared via the reaction of Scheme 2.

In Scheme 2, t, n, A, $R^9$, $R^{12}$, $R^{13}$ and $R^5$ are as above. $R^6$ is an alkyl group having 1 to 7 carbon atoms. $Y^1$ is chloro or bromo.

In the reaction of Scheme 2, the compound of formula VII can be mesylated to furnish the compound of formula VIII via reaction of step (c). Any conventional conditions to carry out mesylation reaction can be utilized. The compound of formula VIII is then heated with the compound of formula IX to produce the compound of formula X. Any of the conditions conventional to produce amino alcohol can be utilized in reaction of step (d).

In the compound of formula X, alcohol is displaced by chloro or bromo by treating the compound of formula X with thionyl chloride, bromine, phosphorus tribromide, carbon tetrabromide and the like to produce the compound of formula XI via reaction of step (e). Any conventional conditions to displace alcohol with chloro or bromo can be utilized to carry out this reaction.

The compound of formula XI can be reacted with a compound of formula II in the presence of a suitable base such as potassium carbonate, sodium hydride, triethylamine and the like. The reaction is carried out in conventional solvents such as N,N-dimethylformamide, tetrahydrofuran, dichloromethane and the like to produce the corresponding compound of formula XII via reaction of step (f).

The compound of formula XII can be converted to the compound of formula XIII via reaction of step (g) by alkylating the compound of formula XII with the compound of formula V. This reaction can be carried out in the presence of approximately a molar equivalent of a suitable base such as lithium hexamethyldisilane or sodium hexamethyldisilane. This reaction is carried out in the same manner as described hereinbefore in connection with reaction of step (b) of Scheme 1. The product can be isolated and purified by techniques such as extraction, evaporation, chromatography, and recrystallization.

The compound of formula XIII is the compound of formula I where $R^1$ is an alkyl group having 1 to 7 carbon atoms. The compound of formula XIII can be converted to the free acid i.e. the compound of formula I where $R^1$ is H by ester hydrolysis. Any conventional method of ester hydrolysis will produce the compound of formula I where $R^1$ is H.

Scheme 2

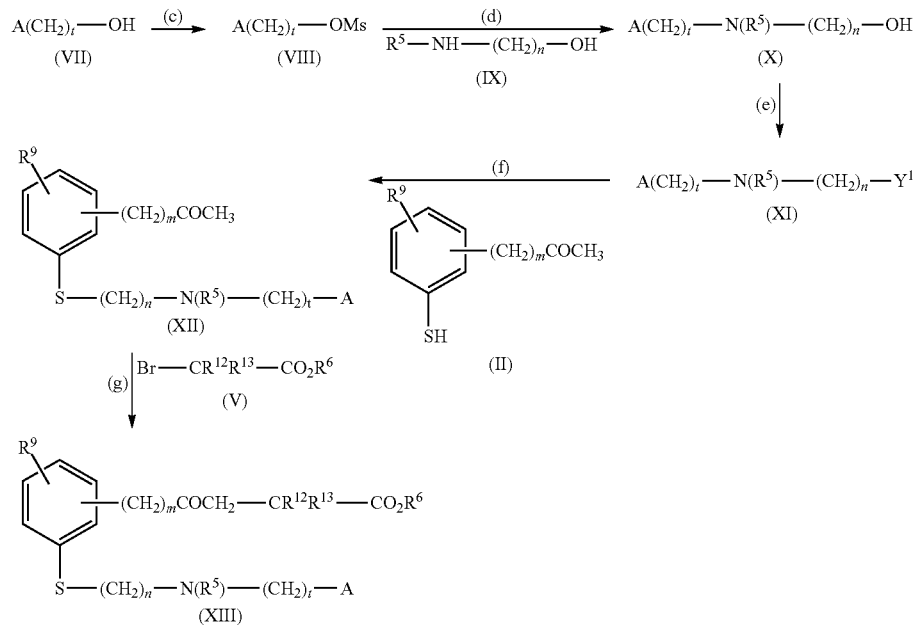

The compound of formula I where X is —$CH_2CH$(NHAc)—, q is 0 or 1, m is 0 or 1, t is 0 or 1, n is 1 or 2, $R^9$ is hydrogen, halo, alkoxy having 1 to 3 carbon atoms or alkyl having 1 to 3 carbon atoms, Q is $OR^1$ where $R^1$ is hydrogen or alkyl having from 1 to 7 carbon atoms and $R^5$ is an alkyl group having 1 to 3 carbon atoms, i.e. compounds of formula:

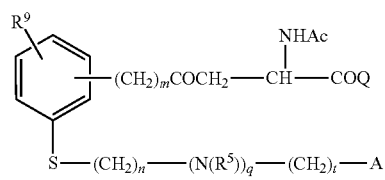

wherein A is described as above, can be prepared via the reaction of Scheme 3.

In the reaction of Scheme 3, t, n, m, A, $R^1$, $R^9$, and $R^5$ are as above. $R^7$ is an alkyl group having 1 to 7 carbon atoms.

The compound of formula IV or XII is prepared in the same manner as described hereinbefore in connection with the reaction of Scheme 1 or 2 respectively.

The compound of formula IV or XII can be converted to compound of formula XIV by selective bromination of the methyl ketone moiety via reaction of step (h) by treating the compound of formula IV or XII with $CuBr_2$. Any selective bromination conditions to convert methyl ketone to 1-bromoketone can be utilized to carry out the reaction of step (h).

7 carbon atoms by esterification of carboxylic acid with compound of formula XVIII using 1,3-dicyclohexylcarbodiimide as dehydrating condensing agent. Any conditions conventional for this reaction can be utilized to carry out the reaction of step (k).

The product can be isolated and purified by techniques such as extraction, evaporation, chromatography, and recrystallization.

The compound of formula XIX is the compound of formula I where $R^1$ is an alkyl chain having 1 to 7 carbon atoms.

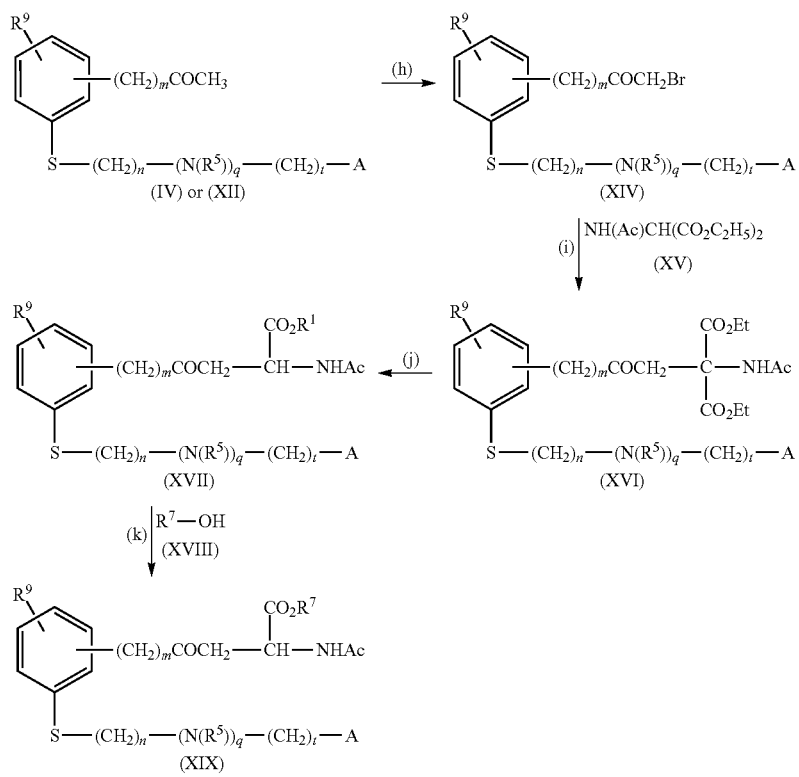

Scheme 3

The compound of formula XIV can be converted to compound of formula XVI via reaction of step (i) by treating the compound of formula XIV with the compound of formula XV. Generally, the reaction is carried out in the presence of approximately a molar equivalent of a suitable base such as sodium ethoxide, or sodium methoxide. The reaction is carried out in conventional solvents such as ethanol, methanol and the like to produce the corresponding compound of formula XVI. Any conventional conditions for this alkylation reaction can be utilized to carry out the reaction of step (i).

The compound of formula XVI can be converted to the compound of formula XVII via reaction of step (j) by de-esterification employing 4 equivalents of sodium hydroxide. Initial mono de-esterification followed by slow hydrolysis of the remaining ethyl ester can be observed. Removal of the solvent and incubation of the residue in acetic acid produced the compound of formula XVII.

The compound of formula XVII is the compound of formula I where $R^1$ is H.

The compound of formula XVII can be converted to compound of formula XIX where $R^7$ is an alkyl chain having 1 to The compound of formula I where X is $—CH_2—$, q is 0 or 1, m is 0 or 1, t is 0 or 1, n is 1 or 2, $R^9$ is hydrogen, halo, alkoxy having 1 to 3 carbon atoms or alkyl having 1 to 3 carbon atoms, Q is $OR^1$ where $R^1$ is methyl or ethyl and $R^5$ is an alkyl group having 1 to 3 carbon atoms, i.e. compounds of formula:

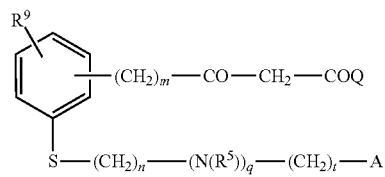

wherein A is described as above, can be prepared via the reaction of Scheme 4.

In the reaction of scheme 4, t, n, m, A, $R^9$, and $R^5$ are as above. $R^{15}$ is ethyl or methyl.

The compound of formula IV or XII (prepared in the same manner as described hereinbefore in the connection of reaction of schemes 1 or 2 respectively) can be treated with a base such as sodium hydride and the like in an appropriate solvent such as N,N-dimethylformamide followed by addition of C-1 or C-2 alkyl carbonate of formula XX to give the compound of formula XXI via reaction of step (1).

The product can be isolated and purified by techniques such as extraction, evaporation, chromatography, and recrystallization.

The compound of formula XXI is the compound of formula I where $R^1$ is ethyl or methyl.

Scheme 4

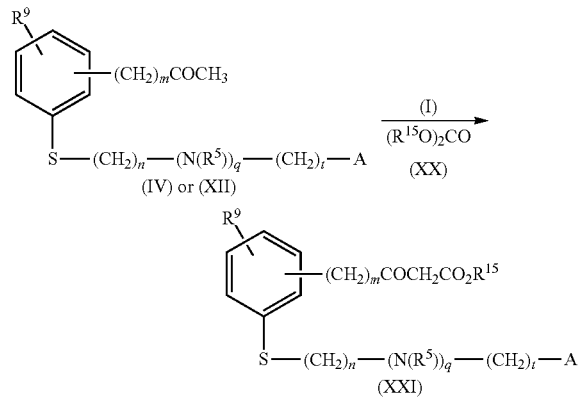

The compound of formula I where X is —$CH_2CH_2$—, q is 0 or 1, m is 0 or 1, t is 0 or 1, and n is 1 or 2, $R^9$ is hydrogen, halo, alkoxy having 1 to 3 carbon atoms or alkyl having 1 to 3 carbon atoms, Q is $NR^{10}R^{11}$ wherein one of $R^{10}$ and $R^{11}$ is hydroxy, and the other is hydrogen, $R^5$ is an alkyl group having 1 to 3 carbon atoms, i.e. compounds of formula:

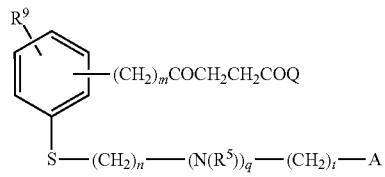

wherein A is described as above, can be prepared via the Reaction Scheme 5. In Scheme 5, t, n, m, A, $R^9$, $R^{10}$, $R^{11}$ and $R^5$ are as above. $R^1$ is H.

The compound of formula VI or XIII (prepared in the same manner as described hereinbefore in the connection with the reaction schemes of 1 or 2 respectively) can be converted to the compound of formula XXII by reaction with chlorinating agent such as thionyl or oxalyl chloride. Generally, the reaction is carried out in solvents such as dichloromethane, N,N-dimethylformamide, or combination of both. The suitable temperature for this reaction can be from 0° C. to 70° C. The intermediate acid chloride can be reacted with hydrazine hydrochloride in the presence of solvents such as mixture of tetrahydrofuran:water (5:1), ethanol and the like by utilizing excess base such as triethylamine, sodium carbonate, potassium carbonate and the like to give the compound of formula XXII via reaction of step (m).

The product can be isolated and purified by techniques such as extraction, evaporation, chromatography, and recrystallization.

The compound of formula I where X is —$CH_2CH_2$—, q is 0 or 1, m is 0 or 1, t is 0 or 1, and n is 1 or 2, $R^9$ is hydrogen, halo, alkoxy having 1 to 3 carbon atoms or alkyl having 1 to 3 carbon atoms, Q is $NR^{10}R^{11}$ wherein $R^{10}$ and $R^{11}$ are hydrogen, $R^5$ is an alkyl group having 1 to 3 carbon atoms, i.e. compounds of formula:

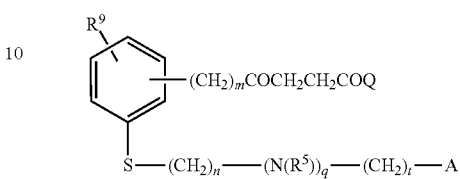

wherein A is described as above, can be prepared via the Reaction Scheme 5.

In Scheme 5, t, n, m, A, $R^9$, $R^{10}$, $R^{11}$ and $R^5$ are as above. $R^1$ is H.

The compound of formula VI or XIII (prepared in the same manner as described hereinbefore in the connection with reaction of scheme 1 or 2 respectively) can be converted to the compound of formula XXIII via reaction of step (n) by first activating the compound of formula VI or XIII with for example, benzotriazol-1-yloxy-tris(dimethylamino)phosphonium hexafluorophosphate or the like in an organic solvent for example, dichloromethane, N,N-dimethylformamide or the like followed by addition of aqueous ammonium hydroxide or ammonia. The reaction is carried out utilizing conventional base such as triethylamine, diisopropylethylamine or the like. Any conditions conventional for the synthesis of amide can be utilized to carry out the reaction of step (n). The product can be isolated and purified by techniques such as extraction, evaporation, chromatography, and recrystallization.

The compound of formula I where X is —$CH_2CH_2$—, q is 0 or 1, m is 0 or 1, t is 0 or 1, and n is 1 or 2, $R^9$ is hydrogen, halo, alkoxy having 1 to 3 carbon atoms or alkyl having 1 to 3 carbon atoms, Q is $NR^{10}R^{11}$ wherein $R^{10}$ and $R^{11}$ are independently hydrogen or alkyl group having 1 to 3 carbon atoms, $R^5$ is an alkyl group having 1 to 3 carbon atoms, i.e. compounds of formula:

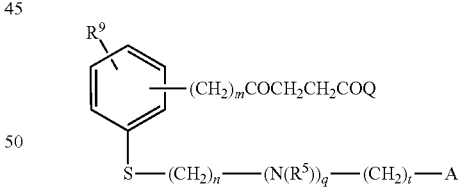

wherein A is described as above, can be prepared via the Reaction Scheme 5.

In Scheme 5, t, n, m, A, $R^9$, $R^{10}$, $R^{11}$ and $R^5$ are as above. $R^1$ is H.

The compound of formula VI or XIII (prepared in the same manner as described hereinbefore in the connection with the reaction of scheme 1 or 2 respectively) can be converted to the compound of formula XXIV via reaction of step (O) by first reaction with chlorinating agent such as thionyl or oxalyl chloride. Generally, the reaction is carried out in solvents such as dichloromethane, N,N-dimethylformamide, or combination of both. The suitable temperature for this reaction can be from 0° C. to 70° C. The intermediate acid chloride can be condensed with the corresponding amine by utilizing conventional base for example pyridine, triethylamine, sodium carbonate, potassium carbonate and the like. The compound of formula VI or XIII can also be condensed with corresponding amine by using dehydrating condensing agent for example dicyclohexylcarbodiimide or the like. Any conditions conventional in converting acid to an amide can be utilized to carry out the reaction of step (o).

The product can be isolated and purified by techniques such as extraction, evaporation, chromatography, and recrystallization.

with a halogen group preferred halogen being bromo or chloro. Appropriate halogenating reagents include but are not limited to thionyl chloride, bromine, phosphorous tribromide, carbon tetrabromide and the like. Any conditions conventional in such halogenation reactions can be utilized to carry out the reaction of step (q). The compound of formula XXVII is the compound of formula III where t is 0 and n is 1.

The compound of formula XXVII can be converted to the compound of formula XXVIII by reacting XXVII with an alkali metal cyanide for example sodium or potassium cya-

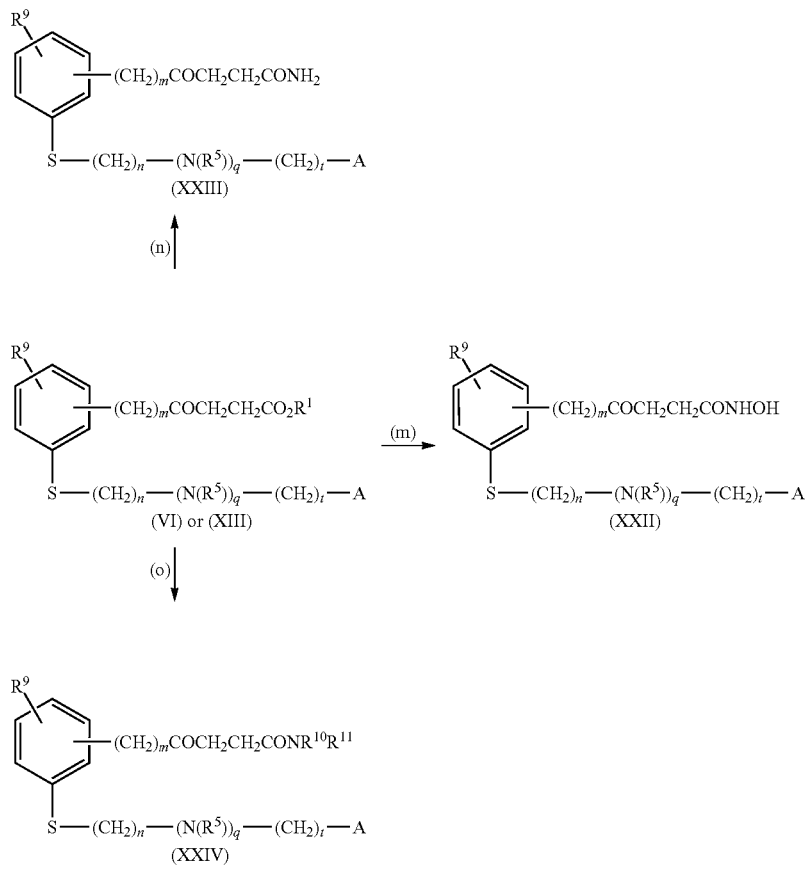

Scheme 5

The compound of formula III where t is 0 or 1, n is 1 or 2, i.e. compounds of formula:

$A(CH_2)_{t+n}$—Y wherein A is described as above, can be prepared via reaction of scheme 6.

In the reaction of Scheme 6, Y is a halo group.

The compound of formula XXV can be reduced to the compound of formula XXVI via reaction of step (p). The reaction is carried out utilizing a conventional reducing agent for example alkali metal hydride such as lithium aluminum hydride. The reaction is carried out in a suitable solvent, such as tetrahydrofuran. Any of the conditions conventional in such reduction reactions can be utilized to carry out the reaction of step (p).

The compound of formula XXVI can be converted to the compound of formula XXVII by displacing hydroxyl group nide. The reaction can be carried out in a suitable solvent, such as dimethyl sulfoxide. Any of the conditions conventionally used in the preparation of nitrile can be utilized to carry out the reaction of step (r).

The compound of formula XXVIII can be converted to the compound of formula XXIX via reaction of step (s) by acid or base hydrolysis. In carrying out this reaction it is generally preferred to utilize basic hydrolysis, for example aqueous sodium hydroxide. Any of the conditions conventionally used in hydrolysis of nitrile can be utilized to carry out the reaction of step (s).

The compound of formula XXIX can be reduced to give the compound of formula XXX via reaction of step (t). This reaction can be carried out in the same manner as described hereinbefore in the connection with the reaction of step (p).

The compound of formula XXX can be converted to the compound of formula XXXI via reaction of step (u) in the same manner as described hereinbefore in connection with the reaction of step (q).

The compound of formula XXXI is the compound of formula III where t is 1 and n is 1.

The compound of formula XXXI can be reacted with diethyl malonate utilizing a suitable base for example sodium hydride to give compound of formula XXXII. The reaction is carried out in suitable solvents, such as N,N-dimethylformamide, tetrahydrofuran and the like. Any of the conditions conventional in such alkylation reactions can be utilized to carry out the reaction of step (v).

The compound of formula XXXII can be hydrolyzed by acid or base to give compound of formula XXXIII via reaction of step (w).

The compound of formula XXXIII can be converted to the compound of formula XXXIV via reaction of step (x) in the same manner as described hereinbefore in connection with the reaction of step (p).

The compound of formula XXXIV can be converted to the compound of formula XXXV via reaction of step (y) in the same manner as described hereinbefore in connection with the reaction of step (q).

The compound of formula XXXV is the compound of formula III where t is 1 and n is 2.

In the compound of formula XXXVII, the nitro group can be reduced to an amino group to give the compound of formula XXXVIII via reaction of step (a'). The reaction can be done using the routine procedures known in the prior art.

The compound of formula XXXVIII can be converted to the compound of formula II via reaction of step (b') by diazotization of amino group followed by substitution with mercapto group. The reaction can be done using the routine procedures known in the prior art.

Scheme 7

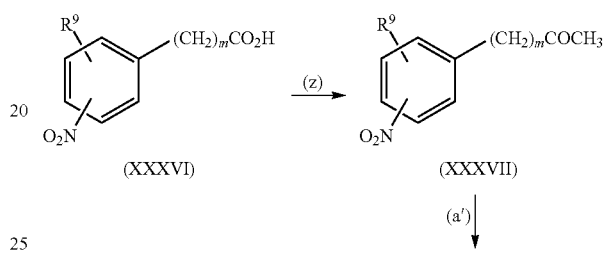

Scheme 6

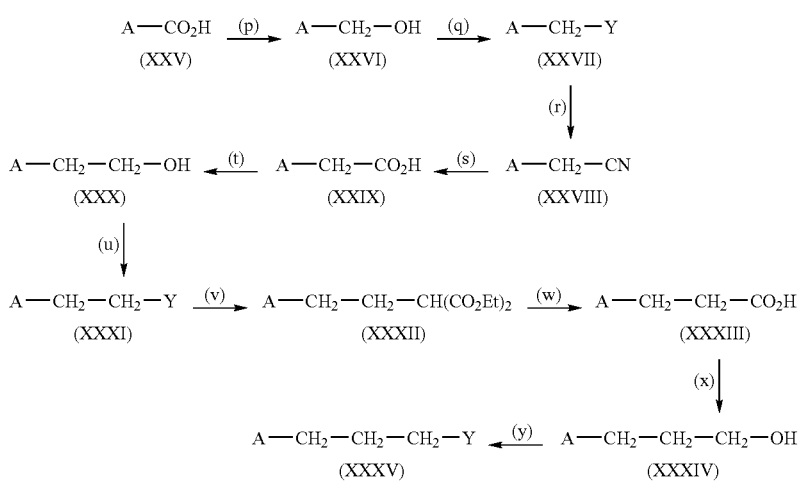

The compound of formula II where m is 0 and $R^9$ is hydrogen, halo or alkyl having from 1 to 3 carbon atoms, i.e. compound of formula:

-continued

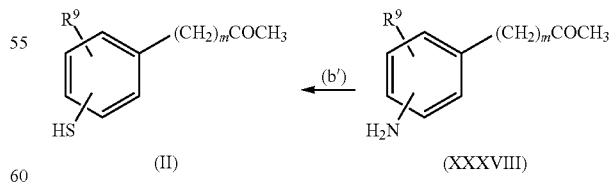

can be prepared via Reaction Scheme 7.

In the Reaction Scheme 7, m and $R^9$ are described as above.

The compound of formula XXXVI can be converted to the compound of formula XXXVII via reaction of step (z) by using method as described in J. Org. Chem. 1983, 48, 1550-1552.

The compound of formula H where m is 0 and $R^9$ is alkoxy having from 1 to 3 carbon atoms, i.e. compound of formula:

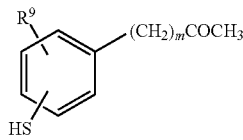

can be prepared via Reaction Scheme 8.

In the Reaction Scheme 8, m and $R^9$ are described as above.

The compound of formula XXXIX can be converted to the compound of formula XL via reaction of step (c') by using method as described in J. Org. Chem. 1983, 48, 1550-1552.

The compound of formula XL can be converted to the compound of formula XLI via reaction of step (d') by alkylating the hydroxy group with an alkyl halide of 1 to 3 carbon atoms. Generally, the reaction is carried out in solvents for example, N,N-dimethylformamide, tetrahydrofuran or the like by utilizing a conventional base such as potassium carbonate, sodium hydride or the like. Any of the conditions conventional for such alkylation reactions can be utilized to carry out the reaction of step (d').

In the compound of formula XLI, the nitro group can be reduced to an amino group to give compound of formula XLII via reaction of step (e'). The reaction can be carried out utilizing the routine procedures known in the prior art.

The compound of formula XLII can be converted to the compound of formula II via reaction of step (f') by diazotization of amino group followed by substitution with mercapto group. The reaction can be carried out utilizing the routine procedures known in the prior art.

The compound of formula II where m is 1 and $R^9$ is hydrogen, halo or alkyl having from 1 to 3 carbon atoms, i.e. compound of formula:

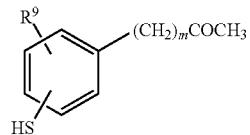

can be prepared via Reaction Scheme 9.

In the Reaction Scheme 9, m and $R^9$ are described as above.

The compound of formula XXXVI can be reduced to the compound of formula XLIII via reaction of step (g') in the same manner as described hereinbefore in connection with the reaction of step (p).

The compound of formula XLIII can be converted to the compound of formula XLIV via reaction of step (h') in the same manner as described hereinbefore in connection with the reaction of step (q).

The compound of formula XLIV can be converted to the compound of formula XLV via reaction of step (i') in the same manner as described hereinbefore in connection with the reaction of step (r).

The compound of formula XLV can be converted to the compound of formula XLVI via reaction of step (j') by using the method of synthesis of phenylacetone as described in J. C. S. Perkin I, 1980, 1555.

In the compound of formula XLVI, the nitro group can be reduced to an amino group to give compound of formula XLVII via reaction of step (k') by utilizing the routine procedures known in the prior art.

The compound of formula XLVII can be converted to the compound of formula II via reaction of step (l') by diazotization of amino group followed by substitution with mercapto group. The reaction can be carried out utilizing the routine procedures known in the prior art.

Scheme 8

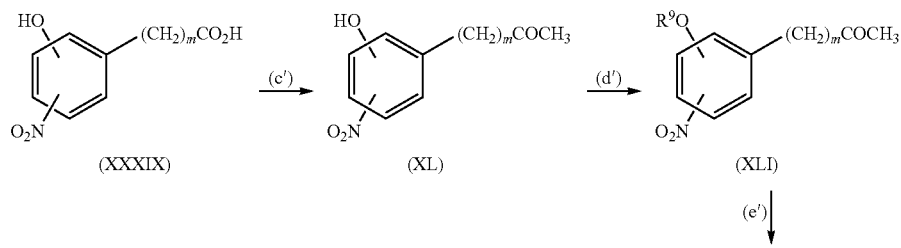

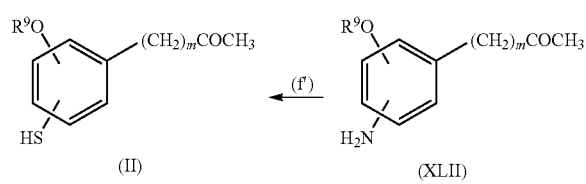

Scheme 9

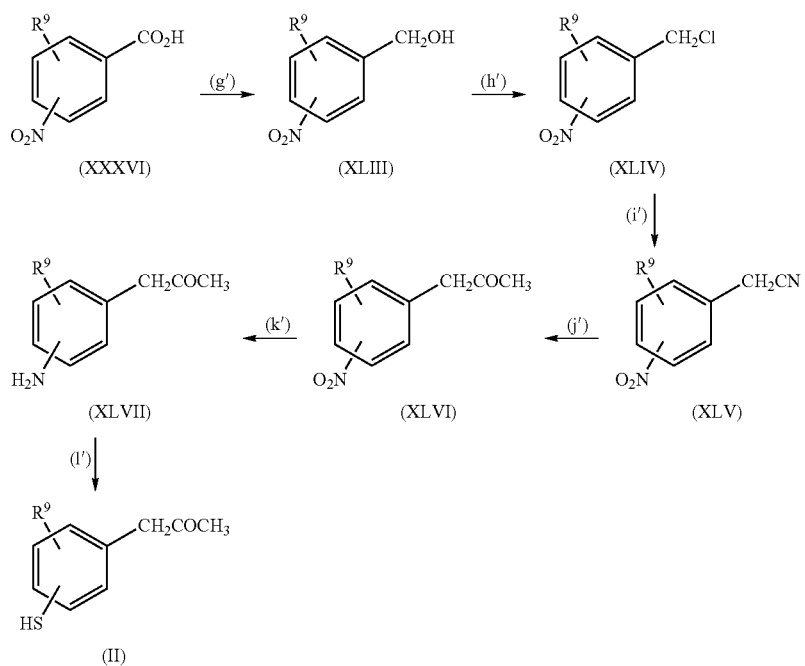

The compound of formula II where m is 1 and $R^9$ is alkoxy having from 1 to 3 carbon atoms, i.e. compound of formula:

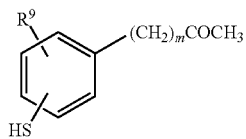

can be prepared via Reaction Scheme 10.

In the Reaction Scheme 10, m and $R^9$ are described as above. $R^{14}$ is alkyl group having from 1 to 2 carbon atoms.

The compound of formula XLVIII can be converted to the compound of formula XLIX via reaction of step (m') by alkylating the hydroxy group with an alkyl halide of 1 to 3 carbon atoms. Generally, the reaction is carried out in solvents for example, N,N-dimethylformamide, tetrahydrofuran or the like by utilizing a conventional base such as potassium carbonate, sodium hydride or the like. Any of the conditions conventional for such alkylation reactions can be used to carry out the reaction of step (m').

The compound of formula XLIX can be reduced to the compound of formula L via reaction of step (n') in the same manner as described hereinbefore in connection with the reaction of step (p).

The compound of formula L can be converted to the compound of formula LI via reaction of step (o') in the same manner as described hereinbefore in connection with the reaction of step (q).

The compound of formula LI can be converted to the compound of formula LII via reaction of step (p') in the same manner as described hereinbefore in connection with the reaction of step (r).

The compound of formula LII can be converted to the compound of formula LII via reaction of step (q') by using the method of synthesis of phenylacetone as described in J. C. S. Perkin I, 1980, 1555.

In the compound of formula LIII, the nitro group can be reduced to an amino group to give compound of formula LIV via reaction of step (r') by utilizing the routine procedures known in the prior art.

The compound of formula LIV can be converted to the compound of formula II via reaction of step (s') by diazotization of amino group followed by substitution with mercapto group. The reaction can be carried out utilizing the routine procedures known in the prior art.

Scheme 10

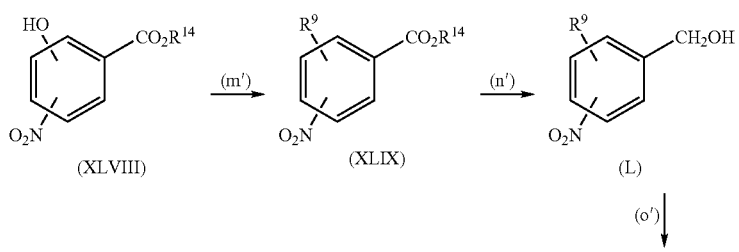

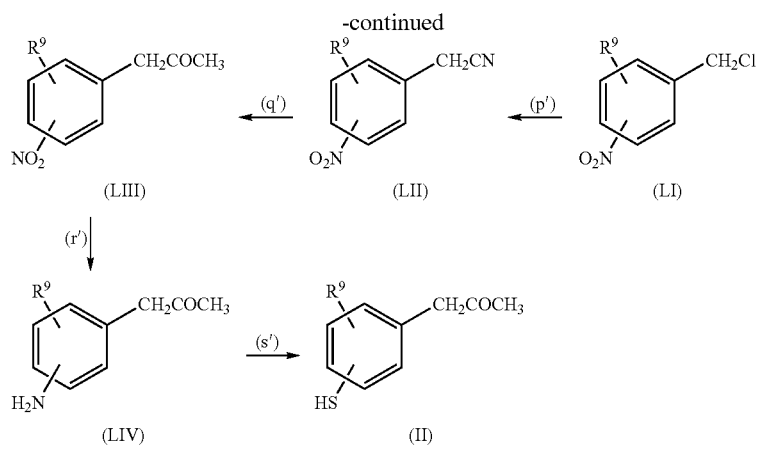

The compound of formula XLVIII where $R^{14}$ is an alkyl group having from 1 to 2 carbon atoms, i.e. compound of formula:

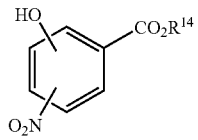

can be prepared via reaction of scheme 11.

In the Reaction Scheme 11, $R^{14}$ is described as above.

The compound of formula XXXIX can be converted to compound of formula XLVIII via reaction step of (t') by esterification with methanol or ethanol. The reaction can be carried out either by using catalysts for example $H_2SO_4$, TsOH and the like or by using dicyclohexylcarbodiimide as the dehydrating condensing reagent. Any of the conditions conventional in such esterification reactions can be utilized to carry out the reaction of step (t').

Scheme 11

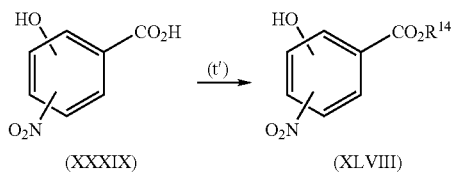

Use in Methods of Treatment

This invention provides a method for treating a mammalian subject with a condition selected from the group consisting of insulin resistance syndrome and diabetes (both primary essential diabetes such as Type I Diabetes or Type II Diabetes and secondary nonessential diabetes), comprising administering to the subject an amount of a biologically active agent as described herein effective to treat the condition. In accordance with the method of this invention a symptom of diabetes or the chance of developing a symptom of diabetes, such as atherosclerosis, obesity, hypertension, hyperlipidemia, fatty liver disease, nephropathy, neuropathy, retinopathy, foot ulceration and cataracts, each such symptom being associated with diabetes, can be reduced. This invention also provides a method for treating hyperlipidemia comprising administering to the subject an amount of a biologically active agent as described herein effective to treat the condition. As shown in the Examples, compounds reduce serum triglycerides and free fatty acids in hyperlipidemic animals. This invention also provides a method for treating cachexia comprising administering to the subject an amount of a biologically active agent as described herein effective to treat the cachexia. This invention also provides a method for treating obesity comprising administering to the subject an amount of a biologically active agent as described herein effective to treat the condition. This invention also provides a method for treating a condition selected from atherosclerosis or arteriosclerosis comprising administering to the subject an amount of a biologically active agent as described herein effective to treat the condition. The active agents of this invention are effective to treat hyperlipidemia, fatty liver disease, cachexia, obesity, atherosclerosis or arteriosclerosis whether or not the subject has diabetes or insulin resistance syndrome. The agent can be administered by any conventional route of systemic administration. Preferably the agent is administered orally. Accordingly, it is preferred for the medicament to be formulated for oral administration. Other routes of administration that can be used in accordance with this invention include rectally, parenterally, by injection (e.g. intravenous, subcutaneous, intramuscular or intraperitoneal injection), or nasally.

Further embodiments of each of the uses and methods of treatment of this invention comprise administering any one of the embodiments of the biologically active agents described above. In the interest of avoiding unnecessary redundancy, each such agent and group of agents is not being repeated, but they are incorporated into this description of uses and methods of treatment as if they were repeated.

Many of the diseases or disorders that are addressed by the compounds of the invention fall into two broad categories: Insulin resistance syndromes and consequences of chronic hyperglycemia. Dysregulation of fuel metabolism, especially insulin resistance, which can occur in the absence of diabetes (persistent hyperglycemia) per se, is associated with a variety of symptoms, including hyperlipidemia, atherosclerosis, obesity, essential hypertension, fatty liver disease (NASH; nonalcoholic steatohepatitis), and, especially in the context of cancer or systemic inflammatory disease, cachexia. Cachexia can also occur in the context of Type I Diabetes or late-stage Type II Diabetes. By improving tissue fuel metabolism, active agents of the invention are useful for preventing or ameliorating diseases and symptoms associated with insulin resistance, as is demonstrated in animals in the Examples. While a cluster of signs and symptoms associated with insulin resistance may coexist in an individual patient, it many cases only one symptom may dominate, due to individual differences in vulnerability of the many physiological systems affected by insulin resistance. Nonetheless, since insulin resistance is a major contributor to many disease conditions, drugs which address this cellular and molecular defect are useful for prevention or amelioration of virtually any symptom in any organ system that may be due to, or exacerbated by, insulin resistance.

When insulin resistance and concurrent inadequate insulin production by pancreatic islets are sufficiently severe, chronic hyperglycemia occurs, defining the onset of Type II diabetes mellitus (NIDDM). In addition to the metabolic disorders related to insulin resistance indicated above, disease symptoms secondary to hyperglycemia also occur in patients with NIDDM. These include nephropathy, peripheral neuropathy, retinopathy, microvascular disease, ulceration of the extremities, and consequences of nonenzymatic glycosylation of proteins, e.g. damage to collagen and other connective tissues. Attenuation of hyperglycemia reduces the rate of onset and severity of these consequences of diabetes. Because, as is demonstrated in the Examples, active agents and compositions of the invention help to reduce hyperglycemia in diabetes, they are useful for prevention and amelioration of complications of chronic hyperglycemia.

Both human and non-human mammalian subjects can be treated in accordance with the treatment method of this invention. The optimal dose of a particular active agent of the invention for a particular subject can be determined in the clinical setting by a skilled clinician. In the case of oral administration to a human for treatment of disorders related to insulin resistance, diabetes, hyperlipidemia, fatty liver disease, cachexia or obesity the agent is generally administered in a daily dose of from 1 mg to 400 mg, administered once or twice per day. In the case of oral administration to a mouse the agent is generally administered in a daily dose from 1 to 300 mg of the agent per kilogram of body weight. Active agents of the invention are used as monotherapy in diabetes or insulin resistance syndrome, or in combination with one or more other drugs with utility in these types of diseases, e.g. insulin releasing agents, prandial insulin releasers, biguanides, or insulin itself. Such additional drugs are administered in accord with standard clinical practice. In some cases, agents of the invention will improve the efficacy of other classes of drugs, permitting lower (and therefore less toxic) doses of such agents to be administered to patients with satisfactory therapeutic results. Established safe and effective dose ranges in humans for representative compounds are: metformin 500 to 2550 mg/day; glyburide 1.25 to 20 mg/day; GLUCOVANCE (combined formulation of metformin and glyburide) 1.25 to 20 mg/day glyburide and 250 to 2000 mg/day metformin; atorvastatin 10 to 80 mg/day; lovastatin 10 to 80 mg/day; pravastatin 10 to 40 mg/day; and simvastatin 5-80 mg/day; clofibrate 2000 mg/day; gemfibrozil 1200 to 2400 mg/day, rosiglitazone 4 to 8 mg/day; pioglitazone 15 to 45 mg/day; acarbose 75-300 mg/day; repaglinide 0.5 to 16 mg/day.

Type I Diabetes Mellitus: A patient with Type I diabetes manages their disease primarily by self-administration of one to several doses of insulin per day, with frequent monitoring blood glucose to permit appropriate adjustment of the dose and timing of insulin administration. Chronic hyperglycemia leads to complications such as nephropathy, neuropathy, retinopathy, foot ulceration, and early mortality; hypoglycemia due to excessive insulin dosing can cause cognitive dysfunction or unconsciousness. A patient with Type I diabetes is treated with 1 to 400 mg/day of an active agent of this invention, in tablet or capsule form either as a single or a divided dose. The anticipated effect will be a reduction in the dose or frequency of administration of insulin required to maintain blood glucose in a satisfactory range, and a reduced incidence and severity of hypoglycemic episodes. Clinical outcome is monitored by measurement of blood glucose and glycosylated hemoglobin (an index of adequacy of glycemic control integrated over a period of several months), as well as by reduced incidence and severity of typical complications of diabetes. A biologically active agent of this invention can be administered in conjunction with islet transplantation to help maintain the anti-diabetic efficacy of the islet transplant.

Type II Diabetes Mellitus: A typical patient with Type I diabetes (NIDDM) manages their disease by programs of diet and exercise as well as by taking medications such as metformin, glyburide, repaglinide, rosiglitazone, or acarbose, all of which provide some improvement in glycemic control in some patients, but none of which are free of side effects or eventual treatment failure due to disease progression. Islet failure occurs over time in patients with NIDDM, necessitating insulin injections in a large fraction of patients. It is anticipated that daily treatment with an active agent of the invention (with or without additional classes of antidiabetic medication) will improve glycemic control, reduce the rate of islet failure, and reduce the incidence and severity of typical symptoms of diabetes. In addition, active agents of the invention will reduce elevated serum triglycerides and fatty acids, thereby reducing the risk of cardiovascular disease, a major cause of death of diabetic patients. As is the case for all other therapeutic agents for diabetes, dose optimization is done in individual patients according to need, clinical effect, and susceptibility to side effects.

Hyperlipidemia: Elevated triglyceride and free fatty acid levels in blood affect a substantial fraction of the population and are an important risk factor for atherosclerosis and myocardial infarction. Active agents of the invention are useful for reducing circulating triglycerides and free fatty acids in hyperlipidemic patients. Hyperlipidemic patients often also have elevated blood cholesterol levels, which also increase the risk of cardiovascular disease. Cholesterol-lowering drugs such as HMG-CoA reductase inhibitors ("statins") can be administered to hyperlipidemic patients in addition to agents of the invention, optionally incorporated into the same pharmaceutical composition.

Fatty Liver Disease: A substantial fraction of the population is affected by fatty liver disease, also known as nonalcoholic steatohepatitis (NASH); NASH is often associated with obesity and diabetes. Hepatic steatosis, the presence of droplets of triglycerides with hepatocytes, predisposes the liver to chronic inflammation (detected in biopsy samples as infiltration of inflammatory leukocytes), which can lead to fibrosis and cirrhosis. Fatty liver disease is generally detected by observation of elevated serum levels of liver-specific enzymes such as the transaminases ALT and AST, which serve as indices of hepatocyte injury, as well as by presentation of symptoms which include fatigue and pain in the region of the liver, though definitive diagnosis often requires a biopsy. The anticipated benefit is a reduction in liver inflammation and fat content, resulting in attenuation, halting, or reversal of the progression of NASH toward fibrosis and cirrhosis.

Pharmaceutical Compositions

This invention provides a pharmaceutical composition comprising a biologically active agent as described herein and a pharmaceutically acceptable carrier. Further embodiments of the pharmaceutical composition of this invention comprise any one of the embodiments of the biologically active agents described above. In the interest of avoiding unnecessary redundancy, each such agent and group of agents is not being repeated, but they are incorporated into this description of pharmaceutical compositions as if they were repeated.

Preferably the composition is adapted for oral administration, e.g. in the form of a tablet, coated tablet, dragee, hard or soft gelatin capsule, solution, emulsion or suspension. In general the oral composition will comprise from 1 mg to 400 mg of such agent. It is convenient for the subject to swallow one or two tablets, coated tablets, dragees, or gelatin capsules per day. However the composition can also be adapted for administration by any other conventional means of systemic administration including rectally, e.g. in the form of suppositories, parenterally, e.g. in the form of injection solutions, or nasally.

The biologically active compounds can be processed with pharmaceutically inert, inorganic or organic carriers for the production of pharmaceutical compositions. Lactose, corn starch or derivatives thereof, talc, stearic acid or its salts and the like can be used, for example, as such carriers for tablets, coated tablets, dragees and hard gelatin capsules. Suitable carriers for soft gelatin capsules are, for example, vegetable oils, waxes, fats, semi-solid and liquid polyols and the like. Depending on the nature of the active ingredient no carriers are, however, usually required in the case of soft gelatin capsules, other than the soft gelatin itself. Suitable carriers for the production of solutions and syrups are, for example, water, polyols, glycerol, vegetable oils and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, coating agents or antioxidants. They can also contain still other therapeutically valuable substances, particularly antidiabetic or hypolipidemic agents that act through mechanisms other than those underlying the effects of the compounds of the invention. Agents which can advantageously be combined with compounds of the invention in a single formulation include but are not limited to biguanides such as metformin, insulin releasing agents such as the sulfonylurea insulin releaser glyburide and other sulfonylurea insulin releasers, cholesterol-lowering drugs such as the "statin" HMG-CoA reductase inhibitors such as atorvastatin, lovastatin, pravastatin and simvastatin, PPAR-alpha agonists such as clofibrate and gemfibrozil, PPAR-gamma agonists such as thiazolidinediones (e.g. rosiglitazone and pioglitazone, alpha-glucosidase inhibitors such as acarbose (which inhibit starch digestion), and prandial insulin releasers such as repaglinide. The amounts of complementary agents combined with compounds of the invention in single formulations are in accord with the doses used in standard clinical practice. Established safe and effective dose ranges for certain representative compounds are set forth above.

The invention will be better understood by reference to the following examples which illustrate but do not limit the invention described herein.

EXAMPLES

Example 1

4-(4-[(2,6-Dimethylbenzyl)-thio]-phenyl)-4-oxobutyric acid

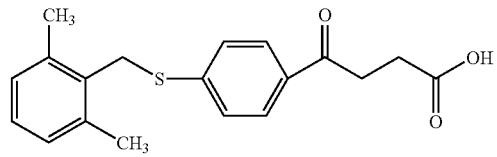

Step A: Preparation of 4'-Mercaptoacetophenone

Synthesized according to procedure as described in WO 94/17054.

Step B: Preparation of 2,6-Dimethylbenzyl Chloride

To a stirred solution of 2,6-Dimethylbenzyl alcohol (9.94 g, 73 mmol) was added thionyl chloride (81.55 g, 685 mmol) at room temperature. The reaction mixture was stirred for 6 hours, concentrated under reduced pressure and used without further purification.

Step C: Preparation of 4-[(2,6-Dimethylbenzyl)-thio]acetophenone

To a stirred solution of NaH (60% in oil, 1.7 g, 51.1 mmol) in dry THF (20 ml) and dry DMF (5 ml) was added 4'-Mercaptoacetophenone (Step A, 5.18 g, 34 mmol) followed by the dropwise addition of 2,6-Dimethylbenzyl chloride (Step B, 4.39 g, 28.4 mmol) diluted in dry THF (5 ml). The reaction mixture was stirred at room temperature for 12 hours, quenched slowly with water at 0° C. The organic layer was extracted with ethyl acetate, washed with brine, dried over $Na_2SO_4$, filtered and concentrated. The purification was done by flash column chromatography on a silica gel column using ethyl acetate:hexane (1:4) to give the title compound.

$^1$H NMR (270 MHz, $CDCl_3$): 2.4 (s, 6H); 2.6 (s, 3H); 4.2 (s, 2H); 6.9-7.1 (m, 3H); 7.4 (d, 2H); 7.9 (d, 2H).

Step D: Preparation of Ethyl 4-(4-[(2,6-dimethylbenzyl)-thio]-phenyl)-4-oxobutyrate To a stirred solution of 4-[(2,6-Dimethylbenzyl)-thio]acetophenone (Step C, 0.693 g, 2.57 mmol) in dry THF (10 ml) and DMPU (3 ml) was added a solution of lithium bis(trimethylsilyl)amide (1.0 M, 3 ml) at −60° C. under argon. After 10 minutes of stirring at −60° C., Ethyl bromoacetate (4.51 g, 3.8 mmol) was added rapidly. The reaction mixture was stirred for an additional 10 minutes and then warmed to room temperature for 4 hours. The crude mixture was taken in EtOAc and washed with water and brine. The aqueous layer was extracted one more time with EtOAc. The combined organic layers were dried over $Na_2SO_4$, filtered, concentrated and purified by flash chromatography on a silica gel column (ethyl acetate:hexane, 1:4) to provide the title compound.

$^1$H NMR (270 MHz, CDCl$_3$): 1.2 (t, 3H); 2.4 (s, 6H); 2.8 (t, 2H); 3.3 (t, 2H); 4.2 (s, 2H); 4.4 (q, 2H); 6.9-7.1 (m, 3H); 7.4 (d, 2H); 7.9 (d, 2H).

Step E: Preparation of 4-(4-[(2,6-Dimethylbenzyl)-thio]-phenyl)-4-oxobutyric acid A solution of Ethyl 4-(4-[(2,6-dimethylbenzyl)-thio]-phenyl)-4-oxobutyrate (Step D, 0.680 g, 2 mmol) in abs ethanol (20 ml) was treated with 1N NaOH (3 ml) at room temperature. The reaction mixture was stirred for 3 hours, acidified with 1M HCl and concentrated. The residue was taken in chloroform and washed with 0.1 M HCl, brine, dried over Na$_2$SO$_4$, filtered and concentrated. The purification was done by flash chromatography on a silica gel column (chloroform:methanol (95:5) spiked with acetic acid) to provide the title compound as off white solid.

$^1$H NMR (270 MHz, CDCl$_3$): 2.4 (s, 6H); 2.8 (t, 2H); 3.3 (t, 2H); 4.2 (s, 2H); 6.9-7.1 (m, 3H); 7.4 (d, 2H); 7.9 (d, 2H).

Example 2

Antidiabetic Effects of Compound CS in db/db Mice

C57BL/Ksola (db/db) mice have a defect in leptin signaling, leading to hyperphagia, obesity, hypertriglyceridemia, and diabetes. Moreover, unlike ob/ob mice on a C57BL/6J background, db/db mice on a C57BLKS background undergo failure of their insulin-producing pancreatic islet cells, resulting in progression from hyperinsulinemia (associated with peripheral insulin resistance) to hypoinsulinemic diabetes.

Male obese (db/db homozygote) C57BL/Ksola mice approximately 8 weeks of age, were obtained from Jackson Labs (Bar Harbor, Me.) and sorted into groups of 7 animals each animals such that the body weights (40-45 g) and serum glucose levels (≧300 mg/dl in fed state) were similar between groups. A minimum of 7 days was allowed for adaptation after arrival. All animals were maintained under controlled temperature (23° C.), relative humidity (50±5%) and light (7:00-19:00), and allowed free access to standard chow (Formulab Diet 5008, Quality Lab Products, Elkridge, Md.) and water.

Groups of mice received daily oral doses of vehicle (1% hydroxypropylmethylcellulose) or Compound CS (60 mg/kg) for 17 days. At the end of the treatment period, blood samples were collected and serum glucose, triglycerides, and free fatty acids were measured.

TABLE I

Effects of Compound CS in the db/db diabetic mouse model

| Groups | Glucose (mg/dL) (±SEM) | Triglycerides (mg/dL) | Free Fatty Acids (μM) |
|---|---|---|---|
| Vehicle (Control) | 812 ± 34 | 352 ± 27 | 2377 ± 119 |
| CS - 60 mg/kg | 593 ± 77 | 150 ± 10 | 2034 ± 195 |

What is claimed is:

1. A biologically active agent, wherein the agent is a compound of the formula:

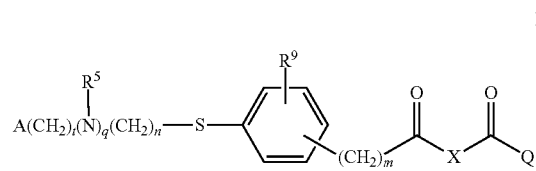

wherein
n is 1 or 2;
m is 0 or 1;
q is 0 or 1;
t is 0 or 1;
R$^5$ is alkyl having from 1 to 3 carbon atoms;
R$^9$ is hydrogen, halo, alkyl having from 1 to 3 carbon atoms, or alkoxy having from 1 to 3 carbon atoms;
A is 2,6-dimethylphenyl; or
cycloalkyl having from 3 to 6 ring carbon atoms wherein the cycloalkyl is unsubstituted or one or two ring carbons are independently mono-substituted by methyl or ethyl; and
X is —CH$_2$—, Q is —OR$^1$ and R$^1$ is methyl or ethyl; or X is —CH$_2$CR$^{12}$R$^{13}$— or —CH$_2$CH(NHAc)- wherein each of R$^{12}$ and R$^{13}$ is independently hydrogen or methyl, Q is OR$^1$ and R$^1$ is hydrogen or alkyl having from 1 to 7 carbon atoms; or X is —CH$_2$CH$_2$— and Q is NR$^{10}$R$^{11}$ wherein one of R$^{10}$ and R$^{11}$ is hydrogen, alkyl having from 1 to 3 carbon atoms or hydroxy, and the other is hydrogen;
or when R$^1$ is hydrogen, a pharmaceutically acceptable salt of the compound.

2. The biologically active agent of claim 1, wherein n is 1; q is 0; t is 0; R$^9$ is hydrogen; and
A is 2,6-dimethylphenyl.

3. The biologically active agent of claim 2, 4-(4-[(2,6-Dimethylbenzyl)-thio]-phenyl)-4-oxobutyric acid.

* * * * *